United States Patent [19]

Kamata

[11] Patent Number: 5,237,600
[45] Date of Patent: Aug. 17, 1993

[54] PATIENT SUPPORT TABLE FOR RADIOGRAPHING WITH X-RAY CAMERA

[75] Inventor: Tomiji Kamata, Tochigi, Japan

[73] Assignee: Kabushiki Kaisha Toshiba, Kawasaki, Japan

[21] Appl. No.: 794,942

[22] Filed: Nov. 20, 1991

[30] Foreign Application Priority Data

Nov. 20, 1990 [JP] Japan .................. 2-312705

[51] Int. Cl.$^5$ ............................. G03B 42/02
[52] U.S. Cl. .................... 378/177; 378/208; 378/209; 5/614; 5/611; 5/612
[58] Field of Search .......... 5/601, 611, 612, 614; 578/177, 187, 183, 209

[56] References Cited

U.S. PATENT DOCUMENTS

| | | | |
|---|---|---|---|
| 3,993,051 | 11/1976 | Maruyama | 5/614 |
| 4,186,917 | 2/1980 | Rais et al. | 5/614 |
| 4,225,125 | 9/1980 | Lee | 5/614 |
| 4,589,642 | 5/1986 | Schnelle et al. | 5/614 |
| 4,953,245 | 8/1990 | Jung | 5/611 |
| 4,959,957 | 10/1990 | Schmale et al. | 5/614 |
| 5,048,069 | 9/1991 | Siczek | 378/197 |
| 5,134,731 | 8/1992 | Quintile et al. | 5/611 |

Primary Examiner—David P. Porta
Assistant Examiner—Kim-Kwok Chu
Attorney, Agent, or Firm—Oblon, Spivak, McClelland, Maier & Neustadt

[57] ABSTRACT

A patient support table utilized when a target such as the circulatory organs of a patient is radiographed with an X-ray camera includes a hydraulic multi-stage piston-cylinder unit of which the top piston is driven in the vertical direction by at least two stages for supporting the patient for a sufficient distal mounted upright on the base of the table; a drive unit for driving the pistons in the axial direction; a multi-stage supporting device of which top moves together with the top of the piston-cylinder unit by at least two stages for supporting an overhanging load exerted by the patient, mounted upright on the base beside the piston-cylinder unit; and, a table top supported by the piston-cylinder unit and the support device, for supporting a patient lying on its surface.

Alternatively a multi-stage cylinder unit of which top is mechanically driven in the vertical direction by at least two stages for supporting the patient for a sufficient distance, is mounted upright on a base of the table; a drive unit for driving the cylinders in the vertical direction; a multi-stage support whose top moves together with the top of the cylinder unit by at least two strokes for supporting an overhanging load caused by the patient, mounted upright on the base beside the cylinder unit; and, a table top supported by the cylinder unit and the supporting device, for supporting a patient lying on its surface.

9 Claims, 9 Drawing Sheets

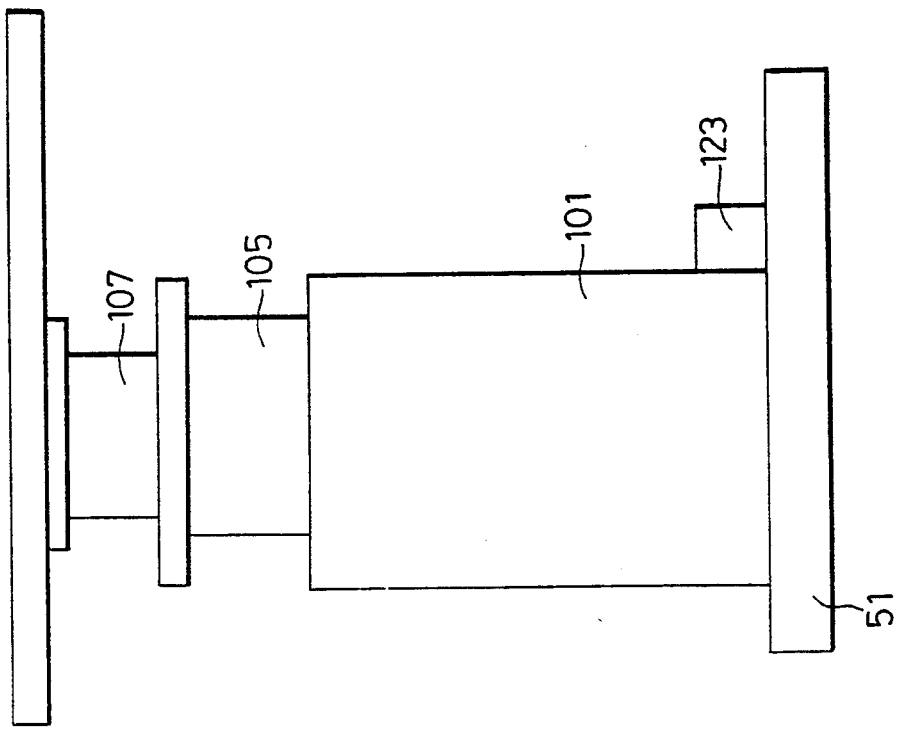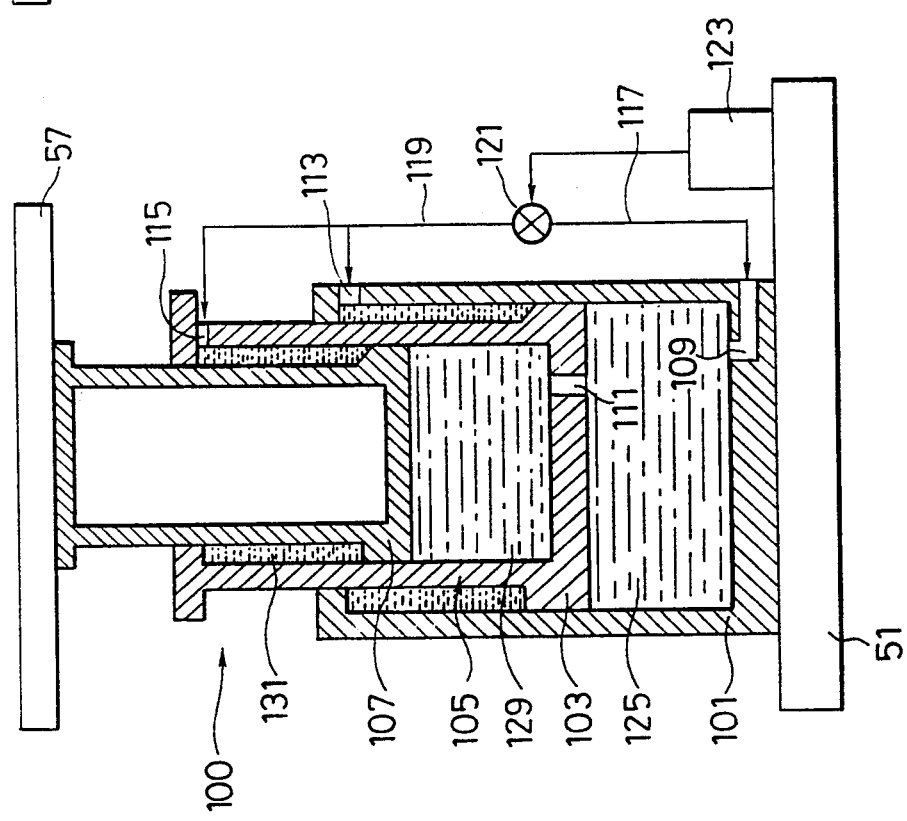

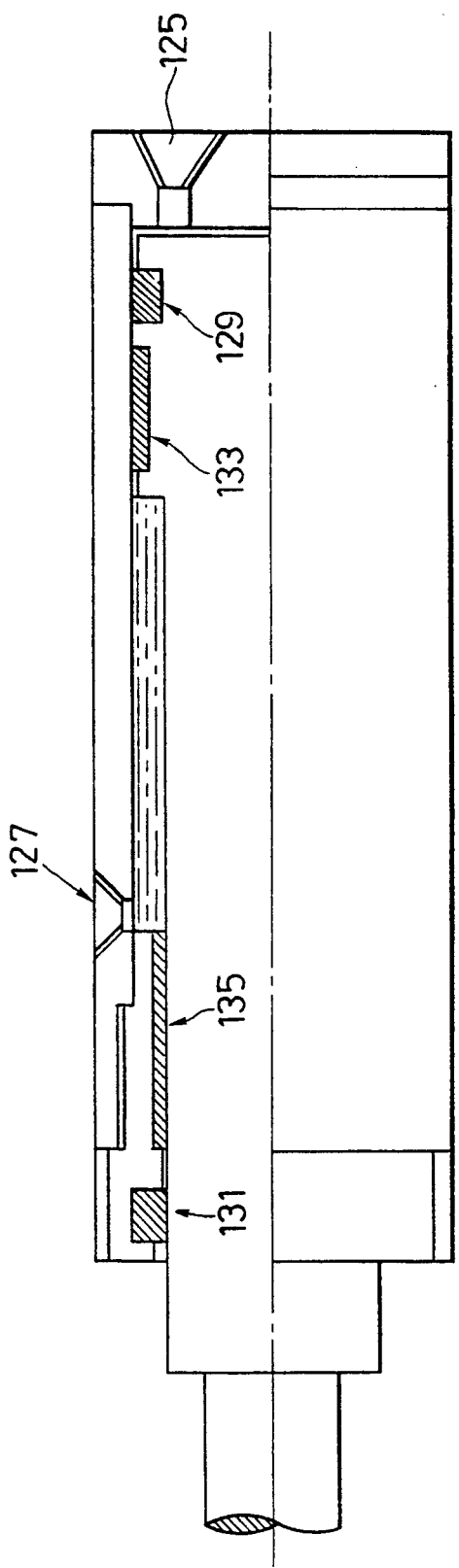

PATIENT SUPPORT TABLE FOR RADIOGRAPHING WITH X-RAY CAMERA

BACKGROUND OF THE INVENTION

1. Field of the Invention

This invention relates to a patient support table utilized when a target such as the circulatory organs of a patient is radiographed with an X-ray camera.

2. Description of the Prior Art

A conventional patient support table uses a lead screw and nut assembly as shown in FIG. 1 for moving a table top 17 in a vertical direction.

The table top 17 is supported by a support pole 15 secured to the nut 13, and driven directionally by turning the lead screw 11 with a drive motor 19. Usually, the support pole 15 is almost the same length as the lead screw 11. Then, both the minimum and maximum heights of the table top are restricted by the length of a lead screw, so that it is impossible to reduce the minimum height or increase the maximum height.

Therefore, this conventional patient support table has the disadvantage that there is insufficient space for a camera unit.

Another conventional patient support table utilized for an X-ray CT device or a MRI device is equipped with a multi-stage link system as shown in FIG. 2. As shown in the figure, the links 31 are secured with a pin joint 33 at one end and constrained with a slider 35 at the other end which requires considerble space in the longitudinal direction of the table.

Therefore, as the link system requires a large amount of space, insufficient space remains to handle an X-ray camera unit. Because of this disadvantage, the link system is not utilized with an X-ray camera unit for radiographing a target such as the circulatory organs of a patient.

SUMMARY OF THE INVENTION

The present invention has been made in an attempt to solve the above-described drawbacks, and therefore has an object to provide a compact patient support table with enough space to handle a camera unit.

A further object of the present invention is to provide a patient support table for which the minimum height of the table top is reduced for convenient loading and for which the table top can be elevated smoothly.

The above-described object and other features of the present invention may be achieved by providing a patient support table comprising:

a hydraulic multi-stage piston-cylinder unit of which the top piston is driven in the vertical direction in at least two stages for supporting the patient for a sufficient distance, mounted upright on the base of the table;

a drive unit for driving the pistons in the axial direction;

a multi-stage supporting means having a top which moves together with the top of the piston-cylinder unit for supporting the table against an overhanging load exerted by the patient, mounted upright on the base beside the piston-cylinder unit; and, a table top supported by the piston-cylinder unit and the support means, for supporting a patient lying on its surface.

Furthermore, a patient support table according to the present invention, comprises:

a multi-stage cylinder unit whose top is mechanically driven in the vertical direction in at least two stages for supporting the patient for a sufficient distance, mounted upright on a base of the table;

a drive unit for driving the cylinders in the vertical direction;

a multi-stage support means whose top moves together with the top of the cylinder unit for supporting the table against an overhanging load caused by the patient, mounted upright on the base beside the cylinder unit; and, a table top supported by the cylinder unit and the supporting means, for supporting a patient lying on its surface.

These and other objects, features and advantages of the present invention will be more apparent from the following description of a preferred embodiment, taken in conjunction with the accompanying drawings.

BRIEF DESCRIPTION OF THE DRAWINGS

The following detailed description is provided for a better understanding of the present invention, with reference to the accompanying drawings, in which:

FIG. 5A is a cross-sectional view of a hydraulic multi-stage piston-cylinder unit of the first embodiment;

FIG. 5B is a front view of the piston-cylinder unit in FIG. 5A;

FIG. 6 is a view of a hydraulic two stage piston-cylinder unit utilized in the first embodiment;

DETAILED DESCRIPTION OF THE EMBODIMENTS

Figure 1:
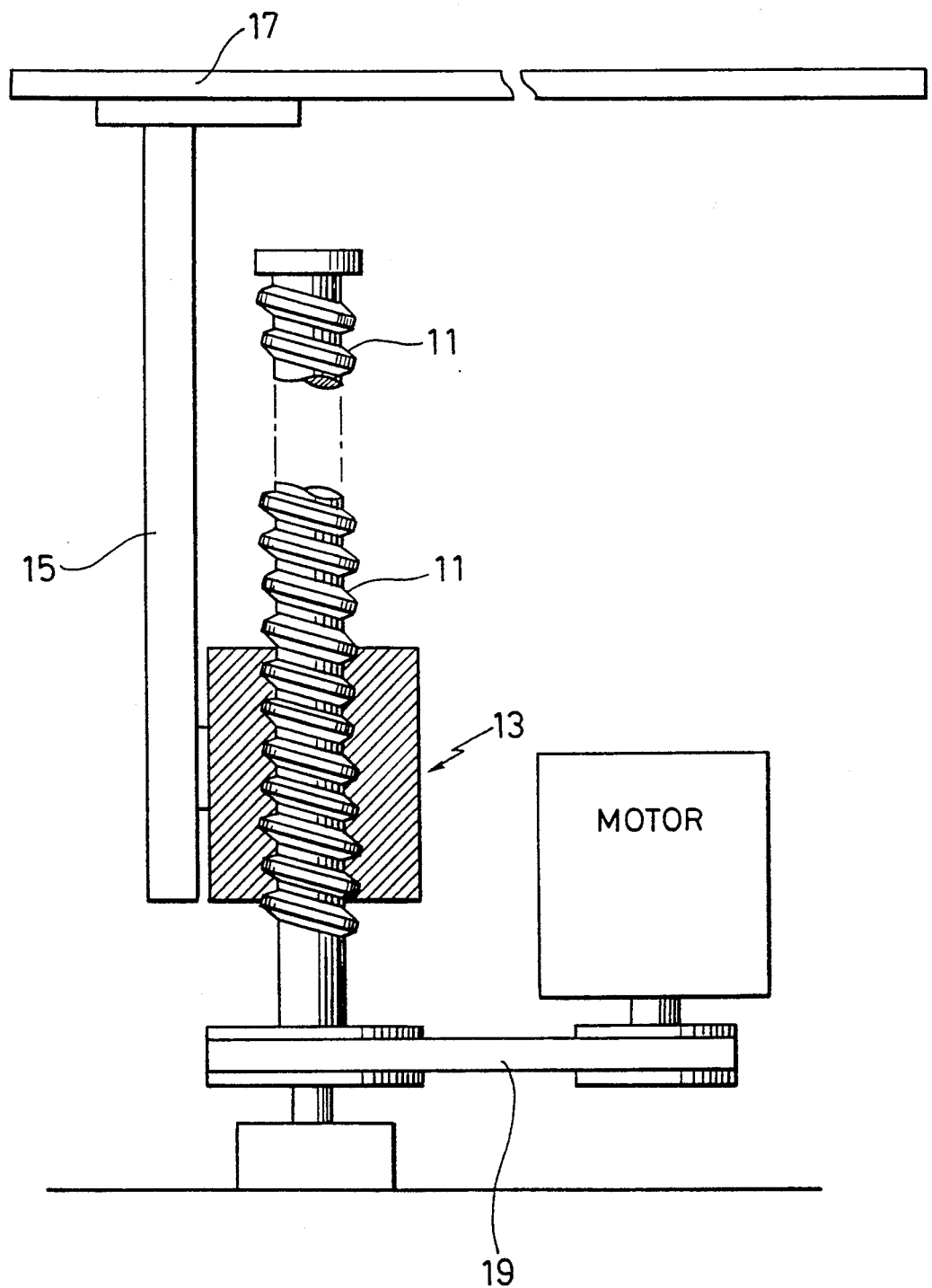
FIG. 1 represents a conventional drive unit for a patient support table comprising a lead screw and nut assembly.
Figure 2:
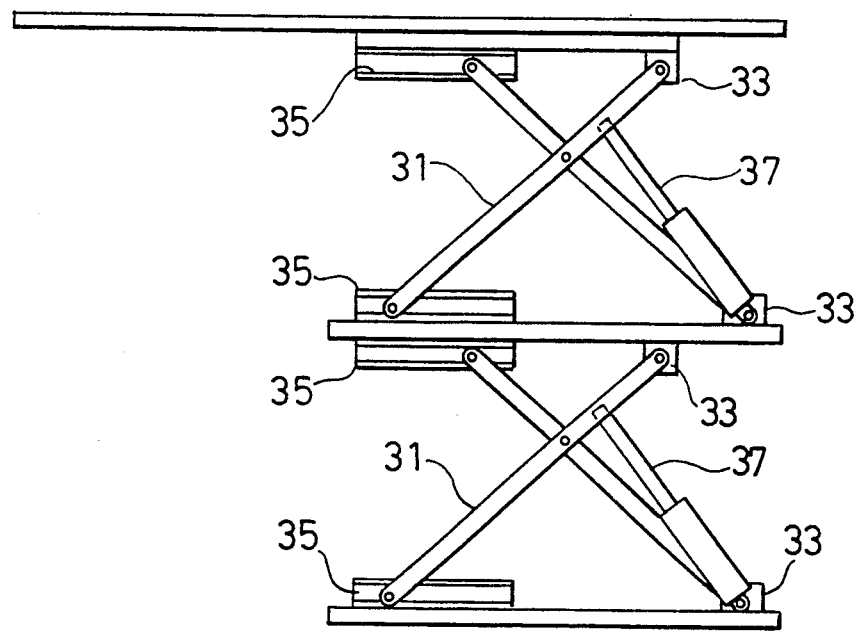
FIG. 2 represents a conventional drive unit of a patient support table comprising links and hydraulic cylinders.

Now referring to FIGS. 3 and 4, an overall arrangement of a patient support table according to a first preferred embodiment of the present invention will be described.

A patient support table 49 is mainly constructed of a hydraulic multi-stage piston-cylinder unit 53, mounted upright on a base 51, for supporting a patient P for a sufficient distance; a drive unit, not shown in the drawings, for vertically driving the pistons by providing compressed fluid to the unit 53; a multi-stage support means 55, mounted upright on the base 51 beside the piston-cylinder unit 53, for supporting an overhanging load exerted by the patient P; and a table top 63 supported by the piston-cylinder unit 53 and the support means 55, for supporting the patient P lying on its surface.

The patient support table 49 further comprises; an X-ray radiograph unit 69 with an X-ray emitter 71, an X-ray camera 73 and a supporter 75, illustrated by two dotted lines. An X-ray emitter 71a and an X-ray camera 73a represent the above-mentioned X-ray emitter 71 and X-ray camera 73, in different positions.

FIG. 5A is a cross-sectional view of the hydraulic two stage piston-cylinder unit 100. This unit 100, as shown in the figure, comprises a first cylinder 101 mounted on the base 51, a first piston 103 formed as one block with a second cylinder 105 which slides on an inside wall of the first cylinder 101 and a second piston 107 placed in the second cylinder 105 for sliding on an inside wall of it.

The first cylinder has oil ports 109, 113 in the bottom and in the top part thereof; a first piston an oil port 111 therein; a second cylinder 105 an oil port 113 in the top part thereof. These oil ports are connected to a switch valve 119 through oil pipes 117, 119 connected to an oil compressing means 123 such as an oil pump or a plunger pump.

The piston-cylinder unit 100 is equipped with sealing rings for maintaining high oil pressures and stoppers for stopping the pistons.

When high pressure oil flows into a chamber 125 through the port 109, the piston 103 moves upward so that the high pressure oil flows into a chamber 129 through a port 111 to move the piston 107 upward, then oil in a part of chambers 127, 131 flows out through a pair of ports 113, 115.

The ports are designed so that the pistons 103, 107 are elevated at almost the same speed when the high pressure oil at a predetermined pressure flows into the port 109.

FIG. 6 shows a hydraulic two stage piston-cylinder unit utilized in this embodiment, and illustrates the first stage of the piston-cylinder mechanism in more detail. Oil port 125, 127, sealing ring 129, 131 and sliding means 133, 135 for reducing friction resistance are shown in the drawing.

Figure 7A:
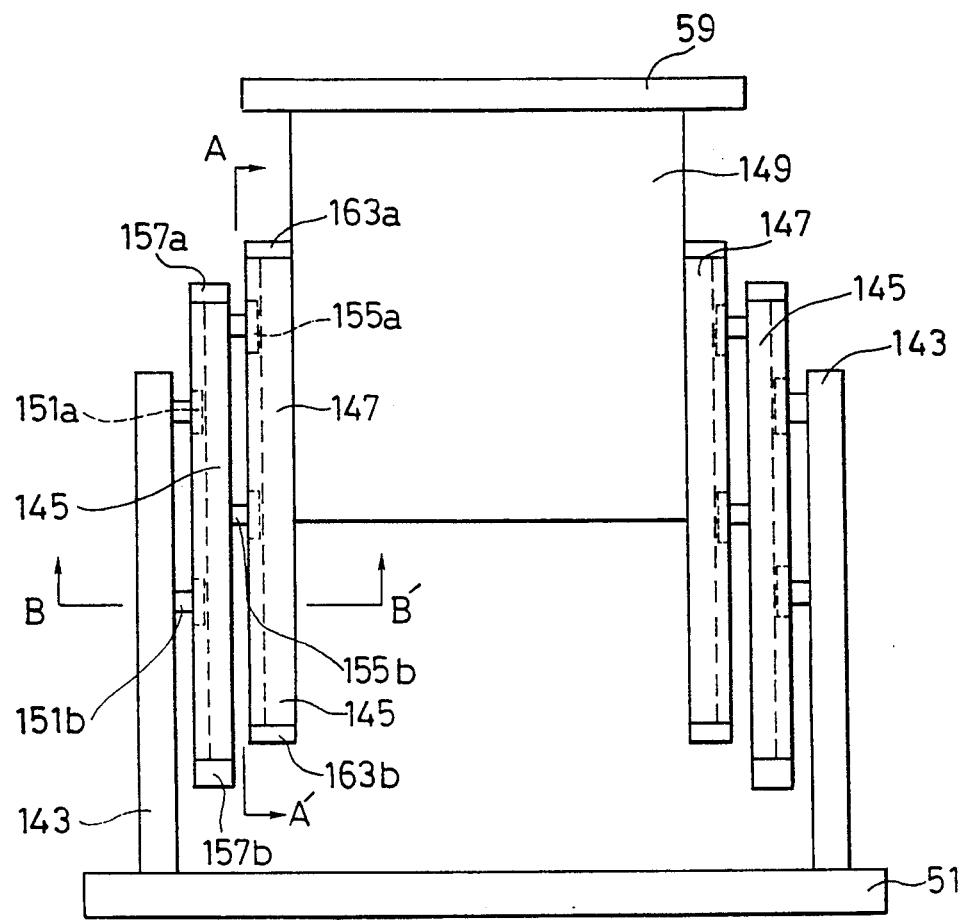
FIG. 7A is a front view of a multi-stage support means of the first embodiment.
Figure 7B:
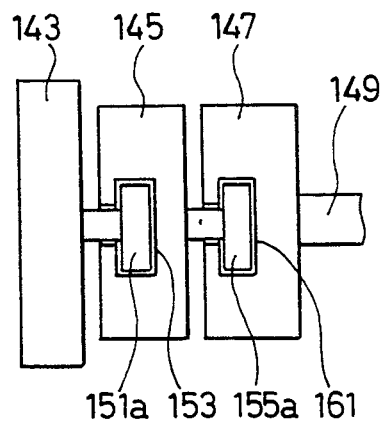
FIG. 7B is a cross-sectional view of the sliding part of the multi-stage support means viewed from arrows B-B' in FIG. 7A.
Figure 7C:
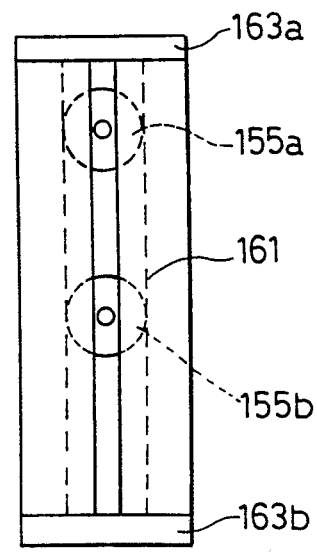
FIG. 7C is a front view of the sliding part of the multi-stage support means viewed from arrows A-A' in FIG. 7A.

FIGS. 7A to 7C show details of a two-stage support means 55 utilized in this embodiment. The support means 55, as shown in the figures, comprises a first support member 143, a second support member 145, a third support member 147 and a connecting member 149. The first support member 143 is equipped with a pair of rollers 151a, 151b at a distance each other, and is mounted upright on the base 51 beside the piston-cylinder unit 53. The second support member 145 is equipped with a guide rail 153 on one side, a pair of rollers 155a, 155b at a distance each other on the other side, and a pair of stoppers 157a, 157b are at each end. The third support member 147 is equipped with a guide rail 161 and a pair of stoppers 163a, 163b, one at each end, and is connected to the connecting member 149.

The rollers 151a, 151b are mounted on the first support member 143 and fitted to the guide rail 153 to move the second support member 145 along the rail 153. The rollers 155a, 155b are also mounted and fitted to the guide rail 161. The two third support members 147 and 147 are both connected to the connecting member 149. Therefore, the connecting member 149 can be moved freely in the vertical direction in two stage strokes, and the support means 55 subject to a bending moment due to an overhanging load exerted by the patient P can also move.

The table top 63 for carrying the patient P thereon is supported by both the hydraulic multi-stage piston-cylinder unit 53 and the multi-stage support means 55.

This embodiment, constructed as above-described, is operated as follows.

Figure 3:
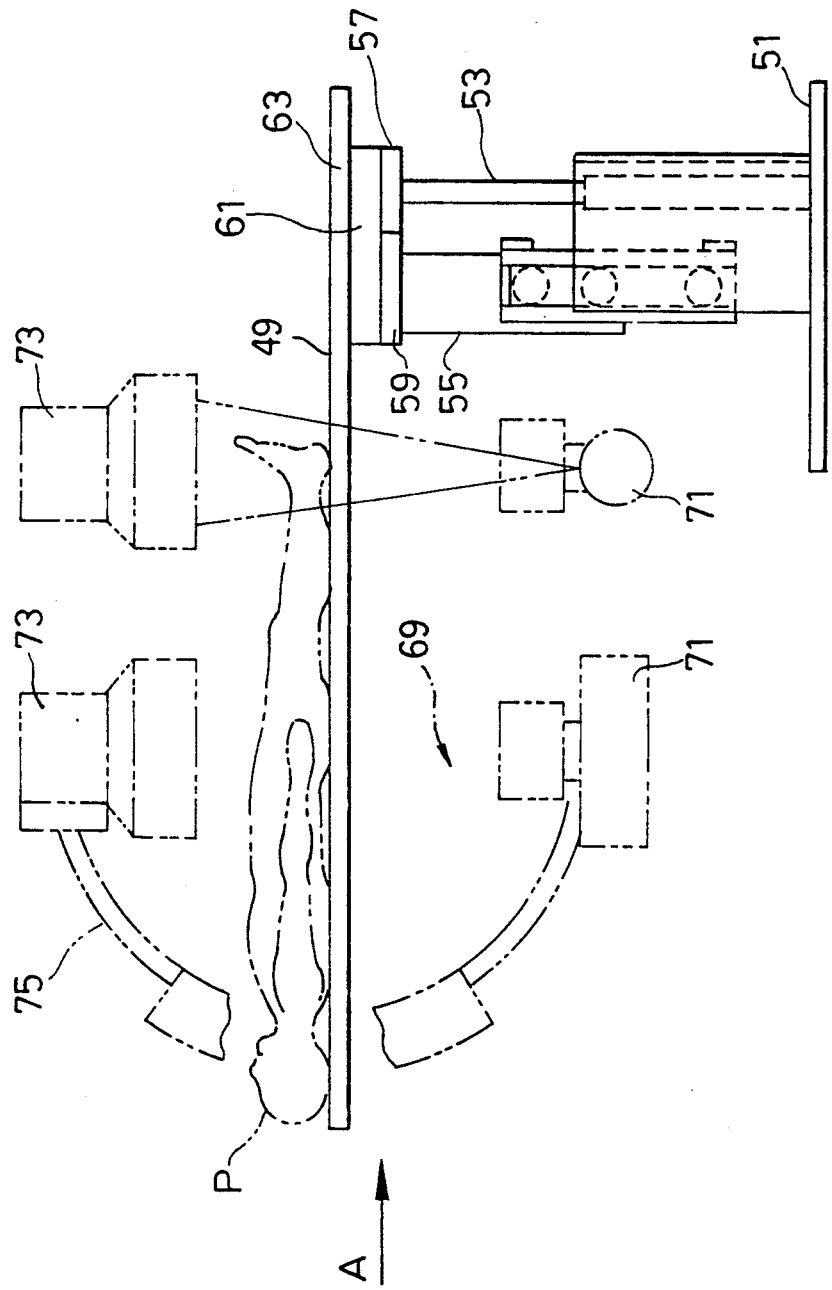
FIG. 3 is a front view of a first embodiment according to the present invention.
Figure 4:
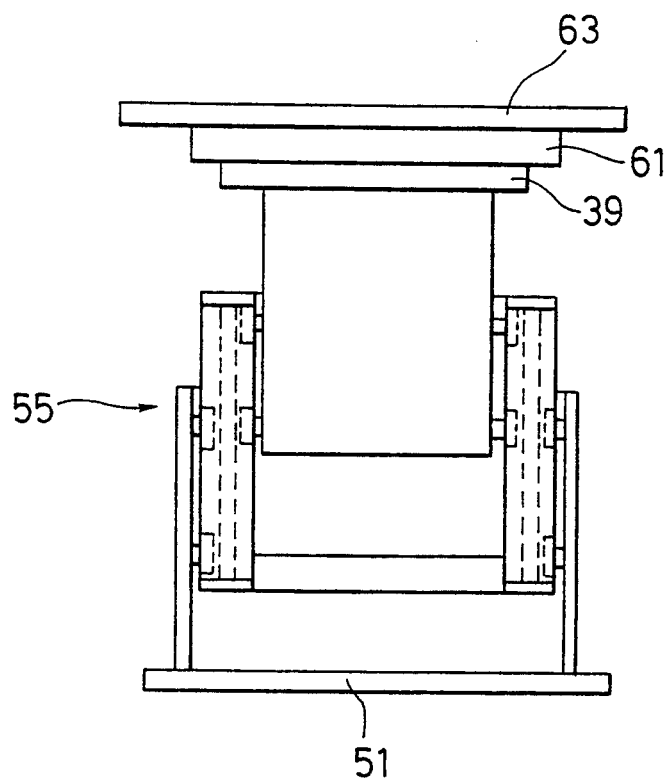
FIG. 4 is a side view of the first embodiment viewed from the arrow A in FIG. 3.

The table top 63 shown in FIG. 3 is positioned at the highest level. In the case where the table top 63, descends, the oil compressing means 123 provides high pressure oil to the ports 113, 115 to press the pistons 103, 107 downward, when the oil valve 121 is switched. The table top 63 connected to the top 57 of the piston-cylinder unit 53, and the top 59 of the support means 55 also move downward as the pistons 103, 107 descend, and they are stopped when both pistons 103, 107 reach the bottom level.

For elevating the table top 63, the procedures are performed in reverse of the case where the table top 63 descends.

The piston-cylinder unit and the support means are arranged as shown in FIG. 3 considering that the moment load applied to the piston-cylinder unit should be minimum because of the necessity of normal contact of the piston with the inside wall of the cylinder.

Figures 8A, 8B, 8C:
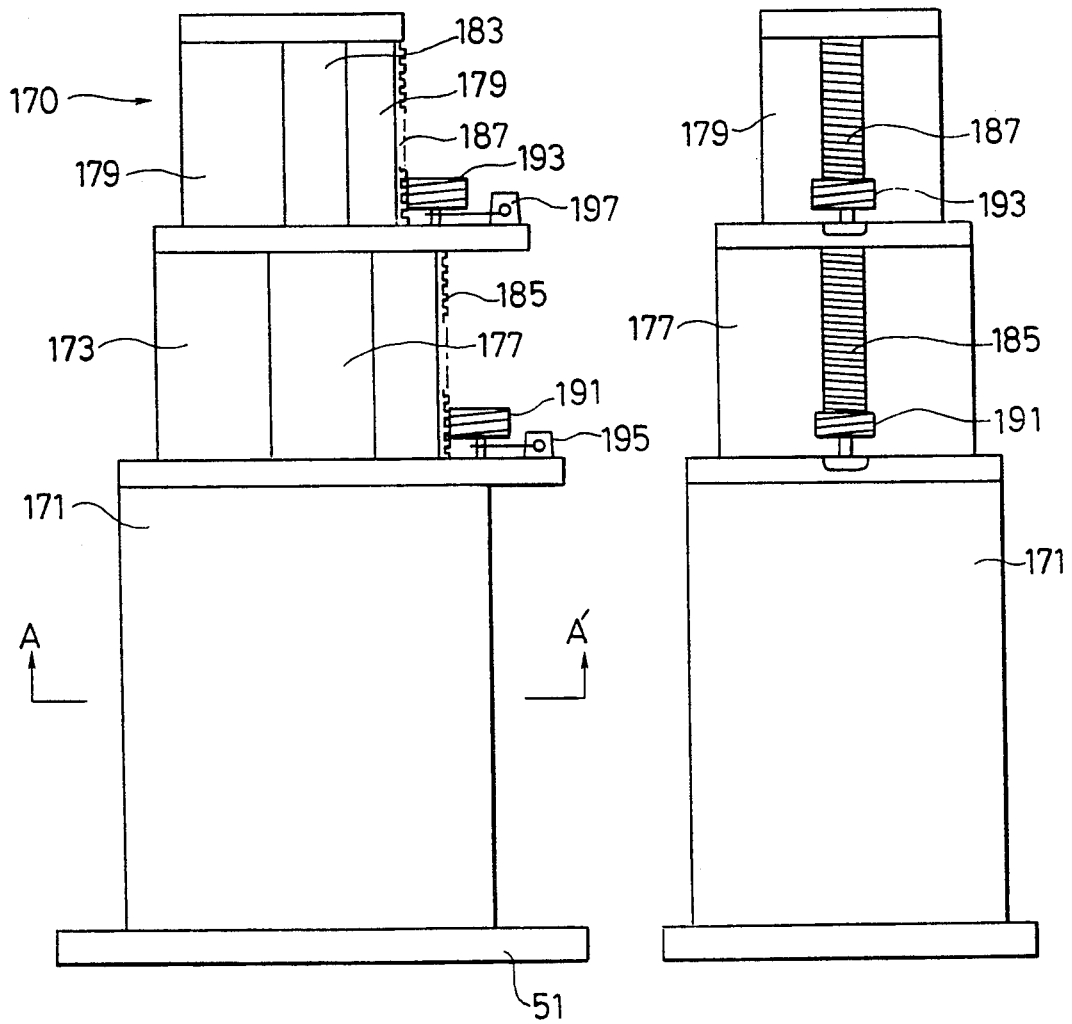
FIG. 8A is a front view of a multi-stage cylinder unit of a second embodiment according the present invention.
FIG. 8B is is a side view of the unit shown in FIG. 8A.
FIG. 8C is a cross-sectional view of the unit viewed from BB' in FIG. 8A.

FIGS. 8A to 8C show a second embodiment according to the present invention. In the second embodiment, a multi-stage elevator 170 having cylinders 171, 173, 179 equipped with rack units 185, 187 is utilized instead of the hydraulic multi-stage piston-cylinder unit 55 of the first embodiment.

The patient support table of the second embodiment comprises a multi-stage cylinder unit 170 for supporting the patient for a totally enough stroke, a pair of drive units 185, 187 for driving the cylinders in the vertical direction, a multi-supporting means for supporting an overhanging load exerted by the patient and a table top for supporting the patient lying on its surface.

The multi-stage unit 170 in the second embodiment, as shown in the drawings, consists of three cylinders and elevating means for elevating the two upper cylinders. The first cylinder 171 is mounted upright on the base 51 of the table. The second cylinder 173 is maintained inside the first cylinder 171 with guides 175, 175 fitted with sliders 177, 177 and driven in the vertical direction by a rack 185 and worm gear 191 assembly. The third cylinder 179 is also maintained inside the second cylinder 173 and driven by a rack 187 and worm gear 193 assembly. The worm gears 191, 193 are rotated by individual motors 195, 197.

Figure 9:
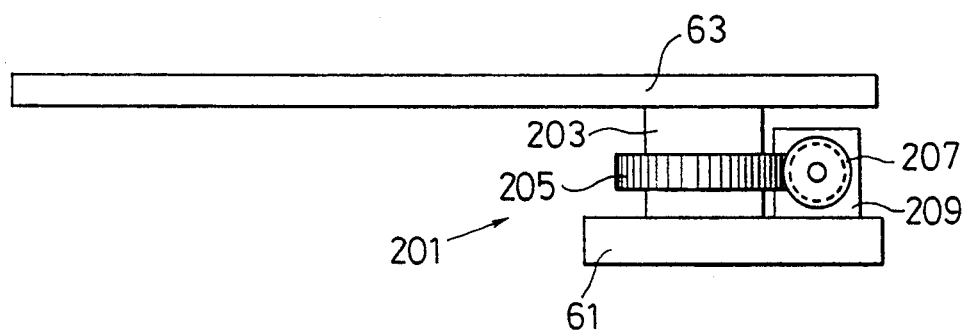
FIG. 9 is a front view of a device for turning a table top.

FIG. 9 shows a rotating device 201 for rotating the table top 63 in the horizontal plane. This device comprises a shaft 203 mounted upright on the reverse side of the table top 63 and held rotatably by the base member 61; a gear 205 attached to the shaft 203, a worm gear 207 engaged with the gear 205, and a rotating means 209 for rotating the worm gear 207.

As the rotating device 201 is constructed with the above-mentioned components, the table top 63 is rotated by driving the rotating means 209.

Figure 10:
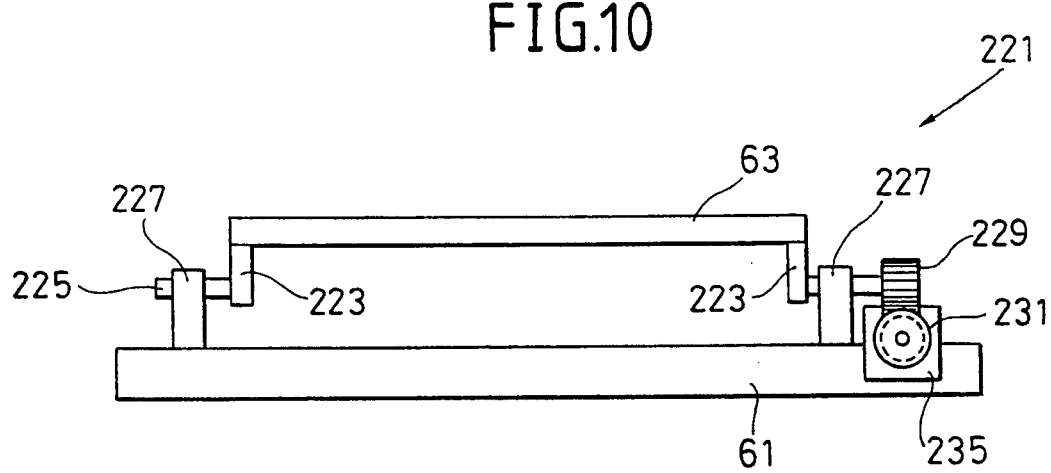
FIG. 10 is a front view of a device for swinging a table top.

FIG. 10 shows a swinging device 221 for swinging the table top 63 in the vertical plane. This device 221 comprises a pair of foot members 223, 223 secured to the reverse side of the table top 63, a pair of shafts 225, 225 each secured to the foot member 223, a support means 227, 227 mounted on the base member 61 for rotatably supporting the shaft 225, a gear 229 attached to one of the shafts 225, a worm gear 231 which engages with the gear 229, and a rotating means 235 for rotating the worm gear 231.

As the swinging device 221 is constructed with the above-mentioned components, the table top 63 is swung by driving the rotating means 235.

Furthermore, the table top 63 is rotated and swung when the table top 63 is equipped with the rotating device 201 and the swinging device 221.

Various modifications will become possible for those skilled in the art after receiving the teachings of the present disclosure without departing from the scope thereof.

For example, although a hydraulic two-stage piston-cylinder unit and a two-stage support means are explained in the above-described embodiments, a three or more stage piston-cylinder unit and a three or more stage supporting means can also be utilized.

As previously described in detail, in accordance with the present invention, since the minimum height of the top board is reduced, the patient is more easily loaded on or off the table top.

Furthermore, according to the present invention, since the patient support table is smaller, the space required to install it is smaller and, therefore, the room space can be more effectively utilized.

In addition, a smoother elevation or descent of the table top is possible when a hydraulic multi-stage piston-cylinder unit is used.

I claim:

1. A patient support table for use with an X-ray camera apparatus, comprising:
   a) an elongate table having a table top for supporting a patient;
   b) a base;
   c) a hydraulic multi-stage piston-cylinder unit mounted to said base, said piston-cylinder unit having a top element drivable in a vertical direction in at least two stages, said top element being mounted to said table top at one longitudinal end of said table for lifting said table top;
   d) drive means for driving said multi-stage piston-cylinder unit; and
   e) a multi-stage support unit mounted to said base and having a top element drivable in a vertical direction in at least two stages, said top element of said support unit being mounted to said longitudinal end of said table top, closer to a longitudinal center of said table top than said top element of said piston-cylinder unit, for bearing a bending moment applied to said table top caused by a patient's weight.

2. A patient support table as claimed in claim 1, wherein each stage of the hydraulic multi-stage piston-cylinder unit moves the top element by a substantially equal distance.

3. A patient support table as claimed in claim 1, wherein the hydraulic multi-stage piston-cylinder unit comprises two pistons and two cylinders, one of said pistons comprising said upper element, including a control device for independently controlling movement of each of the pistons.

4. A patient support table as claimed in claim 1 including a device for turning the table top in a horizontal plane.

5. A patient support table as claimed in claim 1 including is equipped with a device for swinging the table top in a vertical plane.

6. A patient support table as claimed in claim 1 including an X-ray camera system for radiographing the patient.

7. A patient support table for use with an X-ray camera apparatus, comprising:
   a) an elongate table having a table top for supporting a patient;
   b) a base;
   c) a multi-stage cylinder unit mounted to said base, said cylinder unit having a top element drivable in a vertical direction in at least two stages, said top element being mounted to said table top at one longitudinal end of said table for lifting said table top;
   d) drive means for driving said cylinder unit; and
   e) a multi-stage support unit mounted to said base and having a top element drivable in a vertical direction in at least two stages, said top element of said support unit being mounted to said longitudinal end of said table, closer to a longitudinal center of said table top than said top element of said cylinder unit, for bearing a bending moment applied to said table top caused by a patient's weight.

8. A patient support table as claimed in claim 7 including a device for turning the table top in a horizontal plane and swinging it in a vertical plane.

9. A patient support table as claimed in claim 7 including an X-ray camera system for radiographing the patient.

* * * * *